United States Patent
Seare, Jr.

[11] Patent Number: 5,971,961
[45] Date of Patent: *Oct. 26, 1999

[54] NODED CUFFS FOR TRANSCUTANEOUS INTRABODY PROSTHETIC DEVICES

[76] Inventor: William J. Seare, Jr., 3190 E. Chula Vista Cir., Salt Lake City, Utah 84121

[ * ] Notice: This patent issued on a continued prosecution application filed under 37 CFR 1.53(d), and is subject to the twenty year patent term provisions of 35 U.S.C. 154(a)(2).

This patent is subject to a terminal disclaimer.

[21] Appl. No.: 09/082,979

[22] Filed: May 21, 1998

Related U.S. Application Data

[63] Continuation of application No. 08/729,813, Oct. 8, 1996, Pat. No. 5,833,664.

[51] Int. Cl.[6] .............................. A61F 1/00; A61M 25/00
[52] U.S. Cl. ............................................ 604/174; 604/178
[58] Field of Search ................................. 604/174–176, 604/178, 180; 128/DIG. 26

[56] References Cited

U.S. PATENT DOCUMENTS

| | | | |
|---|---|---|---|
| 1,080,934 | 12/1913 | Shackleford | 604/174 |
| 1,109,626 | 9/1914 | Davis | 604/174 |
| 1,198,742 | 9/1916 | Meinecke | 604/174 |
| 3,663,965 | 5/1972 | Lee, Jr. et al. | 604/175 X |
| 3,903,895 | 9/1975 | Alley et al. | 604/178 |
| 4,278,092 | 7/1981 | Borsanyi et al. | 604/175 |
| 5,011,494 | 4/1991 | Von Recum et al. | 623/11 |
| 5,147,318 | 9/1992 | Hohn | 604/174 |
| 5,156,597 | 10/1992 | Verreet et al. | 604/175 |
| 5,484,420 | 1/1996 | Russo | 604/178 |
| 5,713,869 | 2/1998 | Morejon | 604/178 |
| 5,782,800 | 7/1998 | Yoon | 604/54 |

FOREIGN PATENT DOCUMENTS

| | | | |
|---|---|---|---|
| 0 480 653 | 4/1992 | European Pat. Off. | 604/174 |
| 0 589 452 | 3/1994 | European Pat. Off. | 604/174 |

OTHER PUBLICATIONS

Seare, W.J., Pantalos, G.M., Burns, G.L., Mohammed, F., Olson, D.B: Exploration of Use and Advantages of Controlled Porosity Surface Modifications in Material for Vascular and Cardiovascular Application. The Proceedings Cardiovascular Science and Technology Conference, Dec. 2–4, 1991, The Association for the Advancement of Medical Instrumentation.

Seare, W.J., Pantalos, G.M., Burns, G.L., Mohammed, F., Olson, D.B.: The Use of Controlled Porosity Surface Modifications in Artificial Heart Applications. The Proceedings Cardiovascular Science and Technology Conference, page 9, Dec. 12–14, 1992, The Association for the Advancement of Medical Instrumentation.

(List continued on next page.)

Primary Examiner—Wynn Wood Coggins
Assistant Examiner—Sharon Finkel
Attorney, Agent, or Firm—Workman, Nydegger & Seeley

[57] ABSTRACT

This invention relates to methods and apparatus for making and using noded cuffs on transcutaneous or intrabody prosthetic devices, such as catheters, to effect improved stability of the prosthesis/tissue opening site interface. In particular, the noded cuff apparatus of the present invention provides for positioning of the tissue opening site in a manner which facilitates more rapid establishment of a stably biointegrated and well-healed prosthesis/tissue opening site interface. In addition, in accord with the methods of the present invention, non-biointegrated portions of the noded cuff can be simply and easily removed from the underlying prosthetic device to facilitate maintenance of the stably biointegrated interface. Preferably, this removal takes place after a period of time during which the interface has become stably established. In accord with the methods and apparatus of the present invention, thus, infections or healing difficulties at the prosthesis/tissue opening site interface are greatly reduced and a more comfortable and stable interface is more rapidly established and more easily maintained.

20 Claims, 3 Drawing Sheets

OTHER PUBLICATIONS

Seare, W.J., Pantalos, G.M., Burns, G.L., Burt, W.R., Olson, D.B.: Quantitative Bacterial Analysis of Porous and Smooth Implants and Tissue Interfaces in a 169 Day Pneumatic Total Artificial Heart. 1993 Abstracts, p. 12, 39th Annual Meeting, ASAIO Apr. 29, 30 & May 1, 1993.

Seare, W.J., Pantalos, G.M., Burns, G.L., Burt, W.R., Olson, D.B.: Quantitative Bacterial Analysis of Porous, Fabric, and Smooth Non–Blood Contacting Implant Surfaces and Their Tissue Interfaces in a 169 Day Pneumatic Total Artificial Heart Animal Recipient, ASAIO Journal 1993; 39; M668–M647.

Lefton, K.C.: Fighting Infection With New Technology Applied to Catheters, Issues in Infection Control Nephrology News & Issues, Feb. 1995; pp. 18–19.

"Epyemea Drain", American Cystoscope Makers Incorporated, New York, NY, Catalog p. 200, 1952.

NODED CUFFS FOR TRANSCUTANEOUS INTRABODY PROSTHETIC DEVICES

This application is a continuation of application Ser. No. 08/729,813, filed Oct. 8, 1996, which issued as U.S. Pat. No. 5,833,664 on Nov. 10, 1998.

BACKGROUND OF THE INVENTION

1. The Field of the Invention

This invention relates to cuffs for use on transcutaneous or intrabody prosthetic devices at locations where the devices pass through or into a tissue opening site, i.e., a natural or surgically created opening made in the skin or internal body part to accommodate the device. More specifically, the present invention is directed to methods and apparatus for establishing and maintaining more stable interfaces between the cuffed device and the tissue opening site.

2. The Relevant Technology

Many medical situations require relatively long term implantation of a prosthetic device such as a transcutaneous or intrabody catheter. An example of a transcutaneous catheter is a peritoneal catheter used in patients requiring continuous ambulatory peritoneal dialysis (CAPD). An intrabody catheter is a catheter placed entirely within the body such as, for example, a hydrocephalic shunt coursing from the ventricle of the brain to the peritoneum. Such protheses desirably establish and maintain a long-term stable interface with the surrounding tissue and particularly at tissue opening sites, i.e., natural or surgically created openings made in the skin or internal body part to accommodate the prosthesis. Problems with such devices, however, include instability of this prosthesis/tissue opening site interface and accompanying discomfort, prolonged or absent wound healing, and infectious complications which, in a worst case scenario, may prevent proper functioning of the device and/or force removal of the device.

Typically, cuffs, such as DACRON in the form of felts, velours, meshes and weaves, have been utilized at various locations along implanted prosthetic devices, including at the prosthesis/tissue opening site interface, to provide an attachment surface for biointegration with surrounding tissue to thereby stabilize the underlying prosthetic device in a desired position. It has been found, however, particularly at prosthesis/tissue opening site interfaces, that these cuffs may permit contaminants to traverse the site. For example, with CAPD and other transcutaneous catheters, the tissue opening site is generally referred to as the skin exit site. It has been observed that old blood, serum, antiseptic, lint, keratin, etc. tend to accumulate in the portion of the cuff external to the catheter/skin exit site interface. Colonization by bacteria and formation of a bacteria biofilm rapidly occurs within these accumulations. Contamination sometimes progresses through the skin exit site, resulting in a localized exit site infection. Such a local infection can easily become internalized, increasing the difficulty of treatment and the risks to the patient and creating increased morbidity and expense.

With respect to CAPD catheters, for example, infectious complications can be described as falling into several general categories, although it will be appreciated that these problems are interrelated, and may also be thought of as lying along a continuum. Clinical experience has shown that cuffing material, typically DACRON, brought through the skin exit site almost universally becomes an infection site. For this reason, it has become conventional practice to place the DACRON cuff some distance beneath the skin surface, usually 1.0–2.5 cm. Even with this design, however, a common problem is manifested as a fairly localized skin exit site infection, which involves an infection from the location where the catheter enters the skin opening site to, generally speaking, the subcutaneous portion of this first cuff. The next is a tunnel infection, which is an infection involving the first DACRON cuff, if one is applied, and along the tunnel of the subcutaneous course of the uncuffed or underlying catheter up to, or involving, the deep DACRON cuff, which is generally located in the rectus abdominus muscle. Another type of infection is peritonitis, which involves the peritoneal space surrounding the entire catheter within the peritoneum or even beyond the catheter region. It is believed that skin exit site infection can proceed to a tunnel infection and subsequently cause peritonitis, demonstrating the interrelationships of these infections. Many efforts have been directed toward reducing the incidence of skin exit site infection, but little change in infection rates has been observed, despite new advances in cuffing materials, implant techniques and skin exit site care.

Another example of these problems has been observed in connection with artificial heart and heart assist lines, where transcutaneous access is needed for electrical power and possibly venting, or for pneumatic powering of the heart. Here the infection(s) may involve the skin exit site, proceed along the drive line to the pump pocket where it can involve the entire pocket of the pump and subsequently to the valve conduits and vascular grafts. Even though it is rare for these infections to cause the demise of the patient, they do create significant morbidity and expense associated with treatment, and may require operative intervention.

It would be an advancement in the art to provide methods and apparatus permitting establishment and maintenance of a prosthesis/tissue opening site interface with improved stability. In particular, such a stable interface would be less prone to infection and/or wound healing difficulties.

Such methods and apparatus are disclosed and claimed herein.

SUMMARY AND OBJECTS OF THE INVENTION

It is an object of the present invention to provide methods and apparatus permitting establishment and maintenance of a prosthesis/tissue opening site interface with improved stability. In particular, such a stable interface would be less prone to infection and/or wound healing difficulties.

Other objects and features of the present invention will become more fully apparent from the following description and appended claims, or may be learned by the practice of the invention as set forth hereinafter.

This invention relates to methods and apparatus for making and using noded cuffs on transcutaneous or intrabody prosthetic devices, such as catheters, to effect improved stability of the prosthesis/tissue opening site interface. In particular, the noded cuff apparatus of the present invention provides for positioning of the tissue opening site in a manner which facilitates more rapid establishment of a stably biointegrated and well-healed prosthesis/tissue opening site interface. In addition, in accord with the methods of the present invention, non-biointegrated portions of the noded cuff can be simply and easily removed from the underlying prosthetic device to facilitate maintenance of the stable biointegrated prosthesis/tissue opening site interface. Preferably, this removal takes place after a period of time during which the interface has become stably established. In accord with the methods and apparatus of the present invention, infections or healing difficulties at the prosthesis/ tissue opening site interface are greatly reduced and a more comfortable and stable interface is more rapidly established and more easily maintained.

BRIEF DESCRIPTION OF THE DRAWINGS

In order that the manner in which the above-recited and other advantages and objects of the invention are obtained may be understood, a more particular description of the invention briefly described above will be rendered by reference to specific embodiments thereof which are illustrated in the appended drawings. Understanding that these drawings depict only typical embodiments of the invention and are not therefore to be considered to be limiting of its scope, the invention will be described and explained with additional specificity and detail through the use of the accompanying drawings in which.

DETAILED DESCRIPTION OF THE PREFERRED EMBODIMENTS

Figure 1:
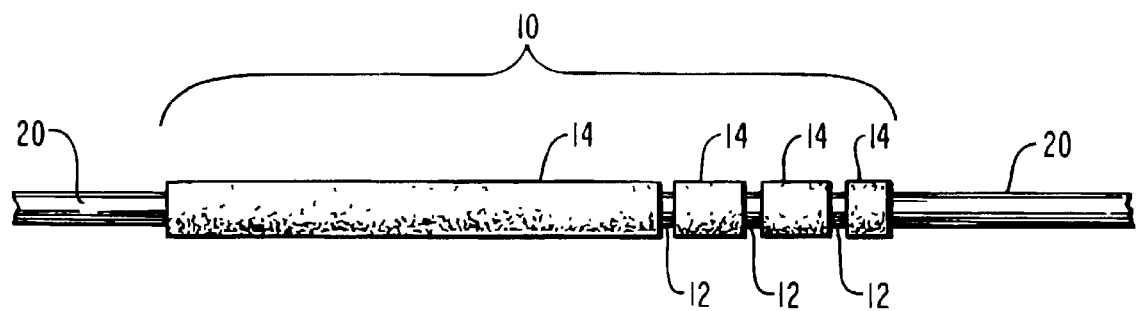
FIG. 1 illustrates a perspective view of a preferred embodiment of a noded cuff in accord with the present invention.

The present invention relates to cuffs for use on transcutaneous or intrabody prosthetic devices at locations where the devices pass through or enter a tissue opening site, i.e., a natural or surgically created opening made in the skin or internal body part to accommodate the device. The cuffs are used to facilitate stabilizing the interface of the device and the tissue opening site. Many medical situations require relatively long term implantation of a prosthetic device such as a transcutaneous or intrabody catheter. An example of a transcutaneous catheter is a peritoneal catheter used in patients requiring continuous ambulatory peritoneal dialysis (CAPD). An intrabody catheter is a catheter placed entirely within the body such as, for example, a hydrocephalic shunt coursing from the ventricle of the brain to the peritoneum. Such protheses desirably establish and maintain a long-term stable interface with the surrounding tissue and particularly at interfaces with tissue opening sites, i.e., natural or surgically created openings made in the skin or internal body part to accommodate the prosthesis.

More specifically, the present invention is directed to methods and apparatus for establishing and maintaining a more stable interface between the cuffed device and the tissue opening site. Although catheters and, particularly, CAPD catheters, are described in the exemplary embodiments herein, it will be appreciated that the methods and apparatus of the present invention have broad applicability to any type of transcutaneous or intrabody prosthetic device which is desired to establish and maintain a stable interface with a tissue opening site.

It has been discovered that rapid establishment of stable prosthesis/tissue opening site interfaces and maintenance of such stable interfaces for prolonged periods can be achieved by replacing conventional cuffs with the noded cuff apparatus of the present invention. In particular, the noded cuff has at least two adjacent cuff segments which extend outwardly from the underlying prosthetic device such as, for example, a catheter. The adjacent cuff segments define a node therebetween. Each node has a first side wall defined by a side of a first adjacent cuff segment and a second side wall defined by a side of the second adjacent cuff segment. Between the walls of the node, at the innermost depth of the node relative to the adjacent cuff segments, is a node termination.

The adjacent cuff segments may be positioned in a spaced apart configuration to define a node therebetween having a node termination at the node innermost depth which is defined by a length of material spanning the distance between the spaced apart side walls of the node (defined by the sides of the spaced apart cuff segments). Alternatively, the adjacent cuff segments may be positioned in a side-by-side touching configuration yet, due to flexibility of the cuff segment material, at least the outer portion of at least one of the cuff segments may be flexed away from the other cuff segment to define a node therebetween having a node termination at the node innermost depth which is defined by the convergence point of the first and second side walls of the node (defined by the sides of the side-by-side cuff segments) when the space is formed between the flexed apart cuff segments.

A node may be a full-depth node which extends the full extent of the outward extension of the adjacent cuff segments such that the node termination occurs at the surface of the underlying prosthetic device. Alternatively, a node may be a partial-depth node which extends only part of the extent of the outward extension of the adjacent cuff segments such that the node termination occurs at a position that is also outwardly extended from the surface of the underlying prosthetic device, although to a lesser extent than the outward extension of the adjacent cuff segments. Thus, any node surrounding an underlying catheter, whether fill-depth or partial-depth, will have a smaller diameter than the more outwardly extending adjacent cuff segments.

The smaller node diameter permits the tissue opening site to have a correspondingly small diameter, the smaller opening will have less likelihood than a larger opening of leakage, bacterial challenge, and other surface area-related problems such as microtrauma. For example, from careful examination of hundreds of failed transcutaneous catheter placements, it appears that one significant cause of failure results from microtrauma at the location where conventional transcutaneous devices exit the skin. Such microtrauma appears to result primarily from movement of the device and/or the skin at the exit site. This movement of the device is translated to a force or movement between the skin and catheter which damages the skin and subcutaneous integrity and hence provides an opening for infection. Positioning of the tissue opening site within a node of the noded cuff of the present invention reduces the extent of such force or movement.

In accord with the methods and apparatus of the present invention, the use of noded cuffs on transcutaneous or intrabody prosthetic devices, such as catheters, results in improved stability of the prosthesis/tissue opening site interface. In particular, a node within the noded cuff, located between adjacent cuff segments of the noded cuff, is positioned at the tissue opening site to permit stable biointegration of the tissue opening site into at least one side wall of the node. Such biointegration, once complete and mature, provides physical stabilization for the catheter.

It has also been observed that use of noded cuffs in accord with the present invention at prosthesis/skin exit site interfaces appears to generate a channeling effect which permits externally applied antiseptic or other beneficial agents to gain more sustained contact with the tissue opening site and the surrounding tissue during the biointegration process. The improved physical stabilization and the more effective application of antiseptic combine to provide a more stable, comfortable and well-healed, and less infection prone, prosthesis/tissue opening site interface than has been observed with conventional cuffs.

In addition, it is a feature of the methods of the present invention to permit simple removal of the noded cuff portions which are external to the prosthesis/tissue opening site interface. This is preferably accomplished following a period of time during which stable biointegration at the prosthesis/tissue opening site interface is established. The noded cuff design permits the external cuff portions to be stripped from the underlying prosthetic device without disruption of the stable biointegrated prosthesis/tissue opening site interface. Removal of the non-biointegrated external cuff portions prevents the accumulation of debris and contaminants, especially bacteria, which routinely occurs within these portions such that a more stable, comfortable and well-healed, and less infection prone, prosthesis/tissue opening site interface can be achieved and maintained over relatively long periods.

FIG. 1 depicts a presently preferred embodiment of the invention. In FIG. 1, the noded cuff 10 of the present invention comprises a cuff surrounding the external surface of an underlying CAPD catheter 20. The noded cuff 10 is positioned on the catheter at a location intended to correspond with the location where the catheter will pass through a skin exit site. The noded cuff 10 comprises four adjacent but spaced apart cuff segments 14 defining three nodes 12 therebetween. It will be appreciated that the number of nodes can be adjusted for specific intended uses. Multiple nodes provide a degree of adaptability for placement of the tissue opening site therein but it will be appreciated that only a single node could be provided.

Referring to the exemplary embodiment of FIG. 1, the use of a plurality of nodes is depicted. As mentioned, although only a single node is needed to interface with a tissue opening site, it is contemplated that multiple nodes are preferable in order to allow more flexibility to the surgeon for placing the underlying prosthesis in a position which is most suitable to the particular patient. The nodes are formed in an area of the noded cuff which is contemplated to be the area where the catheter will interface with a tissue opening site.

For a CAPD catheter, for example, a typical length of the underlying catheter would be about 57 cm and a noded cuff for interfacing with the skin exit site would preferably be formed of 0.25 to 2.5 mm thick cuff material and have a length of about 8 cm applied near the end of the catheter which will be external to the patient. Conventional peritoneal catheters have a deep cuff for positioning at an internal tissue opening site formed in the rectus sheath. Although a noded cuff is illustratively described for the skin exit site interface with a CAPD catheter, it will be appreciated that the deep cuff could also be formed as a noded cuff in accord with the present invention, if desired.

Of the 8 cm noded cuff for interfacing with the skin exit site, about 5.5 cm of that length is intended to be positioned subcutaneously, i.e., internally within the body below the skin exit site. Accordingly, a first node is preferably located about 5.5 cm from the internal end of the noded cuff. Additional nodes, as illustrated in FIG. 1, could be located at selected intervals along the remaining length of the noded cuff where potentially the nodes could come to be external to the body, to provide a degree of adjustability for positioning of the catheter in a position which causes the least tension and stress at the catheter/skin opening site interface and over the internal course of the catheter.

FIGS. 2–8 illustrate enlarged views of portions of various alternative embodiments of noded cuffs in accordance with the present invention. Such alternative embodiments are presented to demonstrate some of the changes that may be made in the noded cuffs of the present invention. One of ordinary skill will appreciate many other changes may be made in view of the teachings contained herein in practicing the present invention.

Figure 2:
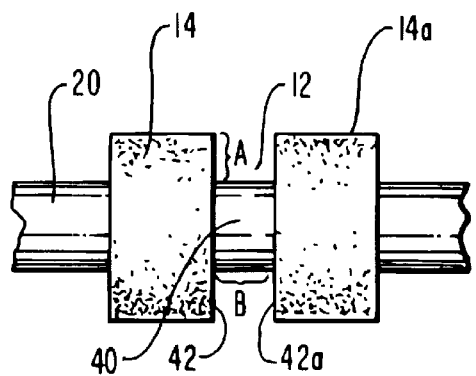
FIG. 2 is an enlarged view of a portion of one embodiment of a noded cuff in accordance with the present invention.

FIG. 2 illustrates an enlarged view of a single node 12 defined by adjacent, spaced-apart cuff segments, designated 14 and 14a, surrounding the underlying catheter 20. For purposes of discussion herein, the depth of node 12 has been designated by the reference letter "A" and the width of the node 12 is designated by the reference letter "B." Node 12 comprises a first side wall 42, defined by a side of adjacent cuff segment 14, and a second side wall 42a, defined by a side of adjacent cuff segment 14a. Because the cuff segments are spaced apart, the node termination 40 at the node innermost depth is defined by a length of material spanning the distance between the first side wall and the second side wall of the node. In addition, because the node 12 is a full-depth node, which extends the full extent of the outward extension of the adjacent cuff segments, the node termination 40 occurs at the surface of the underlying catheter.

Figure 3:
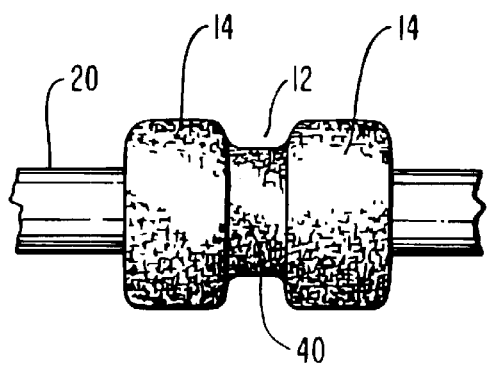
FIG. 3 is an enlarged view of a portion of another embodiment of a noded cuff in accordance with the present invention.

Alternatively, as shown in FIG. 3, a node may be a partial-depth node, which extends only part of the extent of the outward extension of the adjacent cuff segments such that the node termination 40 at the node innermost depth is defined by material other than the underlying catheter surface, e.g., cuff material or another selected material, which also extends outwardly from the surface of the underlying prosthetic device (although to a lesser extent than the outward extension of the adjacent cuff segments).

The node depth and node width may be varied to suit a specific use, with the node depth ranging from about 5 microns to about 3.5 mm, and the node width ranging from about 0.25 mm to about 2.5 mm. For example, for transcutaneous applications such as a CAPD catheter, the node width is preferably selected so as to correspond with the thickness of the skin, or other tissue, at the tissue opening site. This sizing will allow the side walls of the node to generally rest against the tissue of the opening site and assist in stabilizing the tissue within the node. This has been observed to effect more reliable tissue biointegration into the node and the adjacent cuff segment below the skin exit site. Thus, for a CAPD catheter/skin exit site interface, a typical node width range would be about 0.5 mm to about 2.0 mm.

Similarly, the node depth is preferably selected for the particular application, e.g., the depth of a node for a skin exit site interface with transcutaneous CAPD catheter is preferably selected to permit the outer skin layers to migrate fully into the node such that the external surface of the catheter/ skin exit site interface benefits from the protection provided by the outer skin layers. Thus, for a CAPD catheter/skin exit site interface, a typical node depth range would be about 0.25 mm to about 2.5 mm.

For most applications, it is preferred that the cuff material have a surface architecture which promotes tissue biointegration by permitting ingrowth of surrounding tissue into the cuff material. The cuff material preferably comprises a textured, fabric, sintered, or otherwise "porous" surfaced material. A preferred porous cuff material for apparatus in accord with the present invention is the porous material described in Ser. No. 08/156,675, issued as U.S. Pat. No. 5,681,572 on Oct. 28, 1997, the disclosure of which is hereby incorporated by reference. Other material that accomplishes tissue fixation such as, for example, DACRON cuffs in the form of felts, velours, meshes or weaves, and various other types of materials having surfaces permit tissue ingrowth could also be used. Examples of other types of materials include other porous silicone rubbers and polyurethanes and expanded polytetrafluoroethylene. For example, a foamed silicone porous surface, or sintered or spun porous materials could be used. Textured surfaces such as are formed by salt impregnation and dissolution or are formed by known molding, casting, or flowing procedures to create irregular surfaces could also be used.

As previously described, the cuff material in the cuff segments adjacent to a node define the side walls of the node. For partial-depth nodes, the node termination may also comprise cuff material or another selected material. For some applications, the entire node is preferably poroussurfaced to promote tissue biointegration throughout. For other applications, it may be desired to prevent biointegration into some or all regions of the node in which case these regions may have a non-porous or otherwise smooth surface which does not promote tissue biointegration with surrounding tissue.

Although the same cuff material may typically be used throughout the entire noded cuff, it will be understood in light of the teachings herein that different regions of the node and the cuff segments, e.g., different cuff segments or portions of cuff segrnents, adjacent to separate nodes, could comprise different materials or the same material with a different structural configuration resulting in different properties. Accordingly, two adjacent cuff segments, such as cuff segment 14 and cuff segment 14a in FIG. 2, may have different characteristics such as, for example, different porous materials having different pore sizes and pore confiigurations. For example, a stiffer type of cuff material may be used for the side of a cuff segment defining the internal side wall of the node, which will biointegrate with the tissue underlying the skin exit site to provide resistance to the microtrauma of normal catheter movements. A more compliant type of cuffing material may be used for the side of the adjacent cuff segment defining the external side wall of the node, which will rest against the skin surface at the skin exit site, to more comfortably interface with the skin surface and to avoid causing pressure necrosis or compromising blood flow therein.

Figure 4:
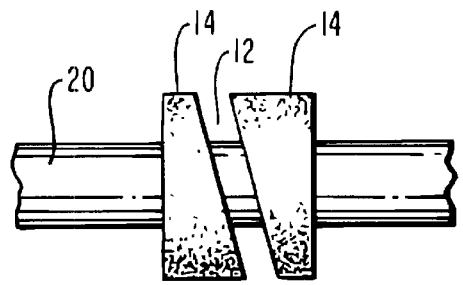
FIG. 4 is an enlarged view of a portion of yet another embodiment of a noded cuff in accordance with the present invention.
Figure 5:
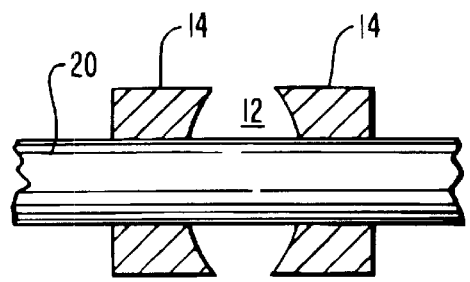
FIG. 5 is an enlarged cross-section view of a portion of another embodiment of a noded cuff in accordance with the present invention.
Figure 6:
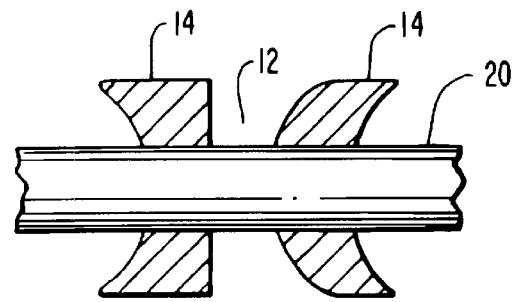
FIG. 6 is an enlarged cross-section view of a portion of another embodiment of a noded cuff in accordance with the present invention.
Figure 7:
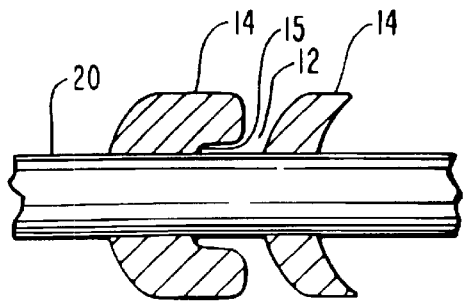
FIG. 7 is an enlarged cross-section view of a portion of another embodiment of a noded cuff in accordance with the present invention.

The positioning of the adjacent cuff segments in a spaced apart or side-by-side touching configuration has been previously discussed. In addition, the specific contour of the sides of the adjacent cuff segments (which define the side walls of the node) may also be varied as desired. For example, the sides of the adjacent cuff segments could be perpendicular to the underlying prosthesis or could be formed in symmetrical or asymmetrical curved or angled contours. Accordingly, for illustrative purposes, a node having angled side walls is shown in FIG. 4, a node having concave side walls is shown in FIG. 5, and a node with asymmetrical side walls is shown in FIG. 6. FIG. 7 depicts a node having parallel curved side walls and having an asymmetrical notch 15 formed in one side wall.

Figure 8:
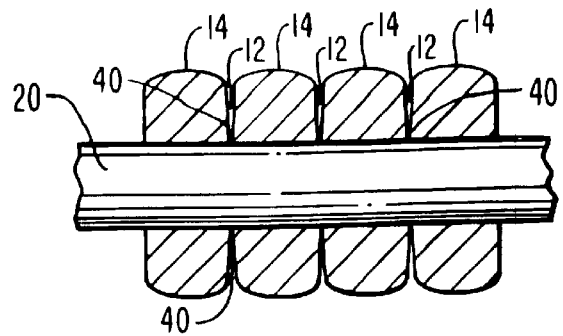
FIG. 8 is an enlarged cross-section view of a portion of another embodiment of a noded cuff in accordance with the present invention.

FIG. 8. illustrates side-by-side touching adjacent cuff segments 14 which can be flexed away from each other to define nodes 12 therebetween. It will be appreciated that the width of nodes defined by side-by-side touching adjacent cuff segments (rather than spaced-apart adjacent cuff segments) is variable because the node width depends on the degree to which the cuff segments are flexed away from each other. Similarly, the depth of the nodes will vary somewhat depending on the degree to which the cuff segments are flexed away from each other. Full-depth nodes are shown in FIG. 8 having node terminations 40 at the node innermost depth defined by the convergence point of the first and second side walls of each node at the surface of the underlying catheter. It will be appreciated that partial-depth nodes could also be formed if the convergence point of the first and second side walls of the nodes occurs at a point that is also outwardly extended from the surface of the underlying catheter.

In addition to physical stabilization of the tissue site opening within the node, it will be appreciated that the noded design permits the biointegrated tissue at the node/ tissue opening site interface to be discontinuous with other cuff segments external to the interface. Tissue biointegration does not progress beyond the node into these other cuff segments. Thus, unlike conventional cuffs, this discontinuity diminishes the potential for a detrimental wicking effect of contaminants and debris which can accumulate in the cuff segments beyond the tissue-biointegrated cuff segments from those non-biointegrated cuff segments into the biointegrated cuff segments.

The noded cuff design of the present invention also appears to provide a channel effect which permits antiseptic solutions or other therapeutic agents applied to the tissue opening site to be channeled into, and retained within, the node. In this manner, such agents have better access to the tissue within the node as the biointegration process proceeds such that stable and infection-free biointegration is facilitated.

It will be further appreciated that the discontinuity caused by the nodes permits cuff material to be removed from the underlying prosthesis in regions external to the biointegrated prosthesis/tissue opening site interface with minimal or no disturbance to that biointegrated site or biointegration process. It is preferred that a period of time to establish a stable biointegration be allowed before removal of nonbiointegrated cuff material be undertaken. This period of time is determined by various factors related to the type of prosthesis and the specific location as well as to situational and patient-related factors and conditions.

The discontinuity further allows for improved control of the biointegration process. Conventional cuff designs (i.e., continuous cuffs rather than the discontinuous, noded cuff designs of the present invention) applied to CAPD catheters and utilizing the porous material described in U.S. Pat. No. 5,681,372 have been observed to permit the biointegration of surrounding subcutaneous tissue into the porous cuff to routinely proceed a small distance along the cuff material outwardly from the skin exit site and, thus, beyond the level of the adjacent dermis and epidermis tissue. The dermal and epidermal skin tissue at the skin exit site, then, grows up to the tissue within the biointegrated cuff but is unable to biointegrate into the cuff because of the biointegrated subcutaneous tissue already present within the cuff. Thus, the biointegrated tissue within the cuff cannot become covered and protected by these dermal and epidermal tissue layers. Rather, this uncovered but biointegrated tissue continues to bleed and continues to be exposed to surface contamination, especially bacteria. The adjacent non-biointegrated cuff material provides a location for debris and contaminants to accumulate and for bacterial biofilm to grow. These contaminants can then gain access through the exposed biointegrated tissue into the underlying tissue and cause infection there.

Figure 9A:
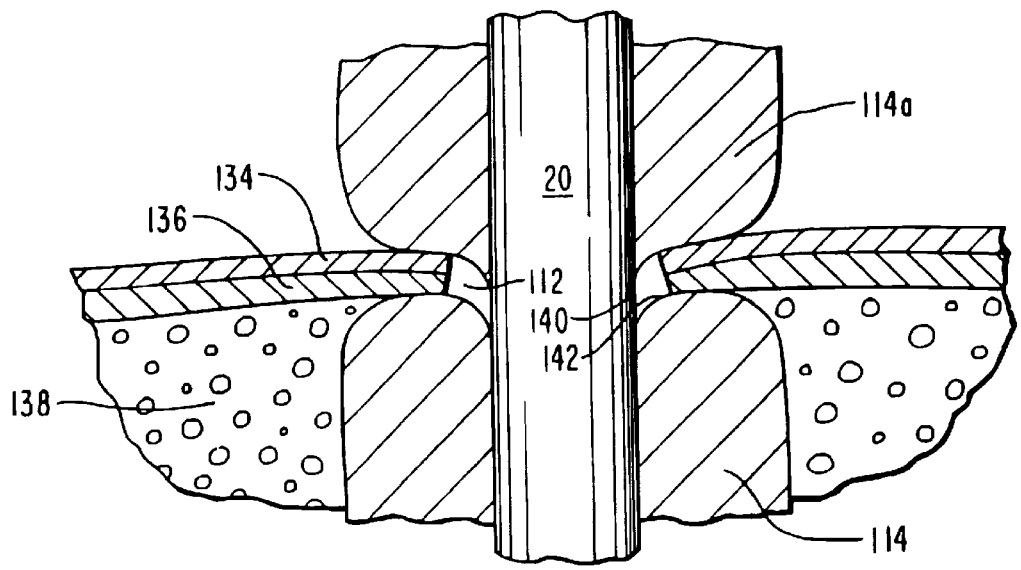
FIG. 9A is a schematic cross-section view of a skin exit site/noded cuff interface in accord with the present invention.
Figure 9B:
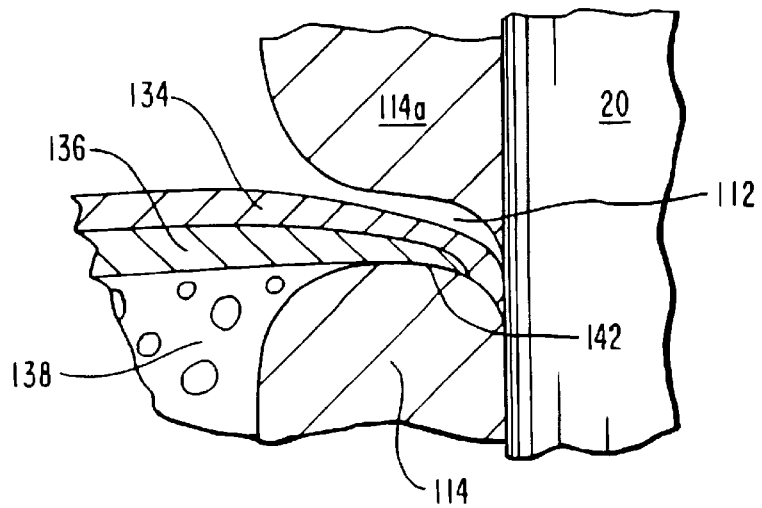
FIG. 9B is an enlarged schematic cross-section view of one side of the skin exit site/noded cuff interface shown in FIG. 9A.

As shown schematically in FIGS. 9A and 9B, the noded cuff design of the present invention provides a barrier to uncontrolled upward and outward tissue biointegration into the cuff and, thus, allows the dermal and epidermal skin tissue to grow over the biointegrated tissue at the skin exit site. FIG. 9A illustrates schematically in cross-section the positioning of a skin exit site within a node of a noded cuff surrounding an underlying CAPD catheter 20. An internal cuff segment 114 and an adjacent but spaced apart external cuff segment 114a define node 112 therebetween. Because the cuff segments are spaced apart, the node termination 140 at the node innermost depth is defined by a length of material spanning the distance between the first side wall and the second side wall of the node. In addition, because the node 112 is a full-depth node, which extends the full extent of the outward extension of the adjacent cuff segments, the node termination 140 occurs at the surface of the underlying catheter 20. As shown, cuff segments 114 and 114a preferably have a parallel curving configuration such that the internal side wall 142 of the node resembles the configuration of the mucosa of the gums interfacing a tooth, the only true human transcutaneous appendage.

In FIG. 9A, the skin exit site is illustrated as having perpendicular cut edges. As described previously, the width of the node 112 is preferably selected to correspond with the depth of the skin tissue layers of the epidermis 134 and dermis 136. Underlying tissue 138, which may comprise subcutaneous or subdermal fat or may also be dermal tissue, is adjacent to internal cuff segment 114. If desired or needed, a small amount of this underlying tissue may be removed at the skin exit site to accommodate the internal cuff segment 114. Also, as described previously, the width of the node 112 is preferably selected to permit the outer skin layers to migrate fully into the node such that the external surface of the catheter/skin exit site interface benefits from the protection provided by the outer skin layers.

In FIG. 9B, an enlarged schematic cross-section view of one side of the skin exit site/noded cuff interface is shown. As biointegration of the underlying tissue 138 into the internal cuff segment 114 proceeds, a stable adherent interface with internal side 142 is created. The epidermis 134 and the dermis 136 within the node biointegrate into the internal side wall 142 of node 112. As healing proceeds, this tissue also migrates to the node termination 140. Thus, as shown, the epidermis and dermis migrates to fully cover the biointegrated underlying tissue within internal cuff segment 114.

It can be seen from FIGS. 9A and 9B that the noded cuff design of the present invention permits stable biointegration of the tissue opening site into the side wall of the node and into the adjacent internal cuff segment. Such biointegration, once complete and mature, provides physical stabilization for the catheter. It can also be seen that the noded cuff design provides a channel effect which permits antiseptic solutions or other therapeutic agents applied to the tissue opening site to be channeled into, and retained within, the node. In this manner, such agents have better access to the tissue within the node as the biointegration process proceeds such that stable and infection-free biointegration is facilitated.

In addition, it is a feature of the methods of the present invention to permit simple removal of non-biointegrated external portions of the noded cuff following stable biointegration at the prosthesis/tissue opening site interface. As can be seen from FIGS. 9A and 9B, this could be easily accomplished by stripping external cuff segment material from the underlying catheter without disrupting the stable biointegrated and healed skin exit site. In this manner, accumulation of debris and contaminants, especially bacteria, which routinely occurs within the non-biointegrated external portions of cuff material, can be prevented such that a more stable, comfortable and well-healed, and less infection prone, prosthesis/tissue opening site interface can be achieved and maintained over relatively long periods.

EXAMPLE 1

A method of using the noded cuff design of the present invention on CAPD catheters is described. The advantages of this method include quicker resolution and healing of the exit site wound and increased biointegration and microvascularity resulting in reduction of capsule formation and scarring at the catheter exit site as well as increased infection resistance and decreased incidence of exit site infections. Decreased incidence of exit site infections should also decrease the incidence of tunnel infections and peritonitis and decrease the rate of catheter loss due to these complications. In addition, the increased biointegration and microvascularity at the exit site should permit more rapid resolution of exit site infections which do occur and the benefit of more likely resolution with local antibiotic therapy to thereby avoid the increased cost, invasiveness. and risk of systemic antibiotic treatment.

Currently marketed peritoneal catheters known as CURL CATH, manufactured by Quinton Instrument Company, Bothell, Wash., have a single DACRON cuff for positioning at the tissue opening site formed in the rectus sheath within the patient's body which is referred to herein as the "deep" cuff. These conventional catheters are modified by having an 8 cm noded cuff, in accord with the present invention, applied to the catheter in the area where the catheter normally exits from the patient. Application of the noded cuff proceeds under appropriate manufacturing conditions, e.g., the cuff is glued on with a suitable adhesive.

The applied noded cuffs are made from porous material produced as described in co-pending patent application Ser. No. 08/156,675. The porous material is composed of premium quality silicone rubbers which are sold and approved for human implantations of thirty days or longer such as products available from Applied Silicone Corporation, Ventura, Calif., and NuSil Silicone Technology, Carpinteria, Calif.

The noded cuffs have an inner diameter comparable to the outside diameter of the CAPD catheter (5 mm). At the end of the cuff intended to be external to the skin exit site, three full-thickness nodes having depths in the range of 0.75–2.5 mm are formed by removal of a 1 mm wide portion of the cuff material from the underlying catheter. The nodes are located at about 0.5 cm, 1.5 cm, and 2.5 cm from the external end of the cuff. This configuration was designed for the surgeon to aim for positioning the skin exit site within the central node but permitting about 1 cm of adjustability in either direction. The skin exit site should be selected such that the distance from the fixed deep cuff position at the rectus sheath opening is suitable for maintaining the catheter in a neutral tension configuration throughout its course. It is preferred that the amount of cuff material external to the skin exit site be in the range of about 5–25 mm. There is usually about 2–3 cm of adjustability in the amount of cuff at the skin exit site because the underlying catheter positioning within the tunnel formed through the tissue can usually be adjusted to this degree.

To form the catheter tunnel, a gently curving, bullet-tipped hollow tunneling instrument or trochar is introduced into the subcutaneous fat at the introductory incision at the rectus sheath, aiming first superiorly and then in a gentle arc along the planned course to the skin exit site. The skin can be manipulated to assist the trochar in its gentle dissection, creating the tunnel within the subcutaneous tissue. Great care is exercised to avoid entering the peritoneum. The diameter of the tunnel should be no larger than the diameter of the catheter and cuffs, and of the same size as the applied noded cuff.

The skin exit site is then made with a dermal biopsy punch of the same diameter as the underlying catheter diameter (5 mm). The punch is pushed and rotated through the skin and subcutaneous tissue, perpendicular to the skin surface until it contacts the tip of the trochar. Care is taken that a full thickness skin excision is made so that when the trocar is pushed through the skin, there will be no stretching damage to the exit site skin. The trochar is then advanced gently through the exit site opening. A small, straight counter incision can be made (superiorly or inferiorly) to expand the hole, if necessary, but this is rarely needed. The opening should be slightly snug but not tight. Some additional dissection of the subcutaneous tissue at the skin exit site is occasionally necessary to assist trochar advancement. This should be gentle and minimal since the immediate subcutaneous tissue and skin exit site will be the barriers to infection from the outside.

The catheter is advanced through the tunnel within the hollow trochar and the trochar is then removed through the skin exit site to deliver the central node of the applied noded cuff to the vicinity of the skin exit site. Final adjustments to the cuff position can be made by pulling the catheter in the desired direction and positioning one of the nodes at the skin exit site. The catheter is flushed with heparinized saline and flow and return of fluids is evaluated. If desired, the catheter may be secured to the skin by placing a typical drain securing suture at least 4 cm from the skin exit site. The external catheter portion is trimmed to the desired length and provided with a catheter occlusion fitting. The subcutaneous tissue of the introductory incision at the rectus sheath are sutured closed. If a counterincision was made, the skin exit site is also sutured closed.

Postoperative skin exit site care is directed toward optimizing and maintaining stable biointegration of the noded cuff material and the surrounding skin exit site tissue. The portion of the noded cuff external to the skin exit site provides the important, but temporary, function of gentle, compliant stabilization of the cuff material at the interface with the skin exit site and subcutaneous tissue allowing biointegration to become established. After biointegration, however, the non-biointegrated external cuff portions become a liability because old blood, serum, lint, keratin, and other materials, including bacteria, can accumulate there. Colonization by bacteria and biofilm formation can occur rapidly. Local antiseptic care and gentle scrapings are used to keep this process in check during the biointegration process. Once stable biointegration has been achieved, however, the external part of the cuff can be removed to provide a more comfortable and less infection-prone exit site. Because of the noded design, this removal can be accomplished with little or no disruption of the biointegrated tissue and the skin exit site.

EXAMPLE 2

A method of using the noded cuff design of the present invention to improve stability of an aqueous humor drainage implant/tissue opening site interface within the eye of a patient suffering from refractory glaucoma is described. Aqueous humor drainage implants are valuable operations in the treatment of refractory glaucoma. The primary purpose is to reduce the chronically elevated anterior chamber pressure within the eye by creating a bypass to the conventional outflow pathways thereby permitting aqueous humor to flow from the anterior chamber to other spaces such as the subconjunctival space.

Reduction of pressure by modern implants is accomplished by shunting of aqueous humor through an open tube device from the anterior chamber to an area of encapsulation around an explant located 8 to 12 mm posterior to the limbus. The purpose of the tube is to drain, in a controlled manner, fluid from the anterior chamber. Essentially all of these devices maintain aqueous humor drainage through an ocular wound surgically created into the subconjunctival space. In such a surgery, the entry tract is made with a 23-gauge needle and the tract is about 2 mm in length. An implanted material referred to as a "seton" is typically used to prevent closure of the surgical wound. The tube attached to the seton is cut at the appropriate length after draping it over the cornea, to measure and select its ultimate length, and it is inserted into the anterior chamber, through the opening made in the limbus.

Complications and failures occur when the seton and/or anterior drainage tube migrate out of the desired position within anterior chamber of the eye. Movement of the tube may also cause kinking which prevents proper drainage. Less commonly, the tube may migrate to, and sometimes through, the endothelium of the cornea and even through the entire thickness of the cornea. Constant tube-corneal contact results in progressive corneal endothelial cell loss. In addition, tube touching of the lens may be associated with the formation of cataract.

Because of the delicate tissues, the small sizes and exacting placements required for the successful performance of these devices, it would be beneficial to establish and maintain a more stable prosthesis/tissue opening site interface and thereby avoid or minimize complications due to migration of the implanted devices. For example, a noded cuff in accord with the present invention could be placed around the entire length of the anterior drainage tube. Nodes could be positioned at spaced intervals along the entire cuff or only where the tube might ultimately come to lie at the anterior chamber tissue opening site, i.e., either at a full-thickness limbal entry tract or at the end of a lamella scleral flap. This opening into the anterior chamber is analogous to the skin exit site of a CAPD catheter except that there is aqueous fluid present within the chamber. Positioning of the anterior chamber tissue opening site within a node of the noded cuff would help to stabilize the tube within the anterior chamber. In addition, the remaining portions of the noded cuff also biointegrate into the surrounding tissue, especially the limbal conjunctiva, sclera and episcleral tissues, to further stabilize the tube position.

Like CAPD catheters, the material most frequently used for anterior chamber drainage tubes is silicone rubber. The outer diameters of anterior chamber tubes generally vary from 0.64–0.58 mm and the internal diameter is generally 0.3 mm. Because the tubes are so small, and because it is desirable to promote biointegration along much of the entire length, the noded cuff is preferably applied to the entire length of these devices rather than only at the region which passes through a tissue opening site. The cuff material used and the depths and widths of the nodes within a noded cuff to be applied to an aqueous humor drainage implant are selected to be suitable for this application. For example, the preferred cuff material would be textured or otherwise porous-surfaced silicone rubber to facilitate biointegration. The pore sizes within the cuff material, however, are preferably much smaller than on the cuff material suitable for subcutaneous tissue biointegration at a CAPD catheter skin exit site. Generally, the sizes of the textured surface irregularities or the porous-surfaced pore sizes within cuff material to be applied to an aqueous humor drainage implant would be of the order of cellular element sizes, or 3–5 microns, up to several hundred microns. The cuff thickness would be from about 0.10 mm to several millimeters. The width of the nodes would be variable from very slight (for side-by-side touching adjacent cuff segments) up to about 1 or 2 millimeters. The nodes could be full-depth nodes or partial depth nodes with a depth range similar to the cuff thickness, i.e., from about 0.10 mm to several millimeters.

EXAMPLE 3

Another application of the noded cuff of present invention would be with a total artificial heart, such as a Utah U-100. The pneumatic drive lines which power the ventricle of the heart must exit through a transcutaneous exit site in the patient's skin and be attached to a pneumatic driver. Typically, the total length of a drive line is about 38 cm, the outer diameter of the drive line is 9 mm and the inner diameter is 6 mm, and the wall thickness is 1.5 mm. The drive lines and the ventricle are made of BIOMER, which is a LYCRA or SPANDEX-like polyurethane. Typically, about 28 cm of the drive line, for placing within the patient's body and for surrounding the drive line skin exit site, is covered with a polyester velour. The remaining approximately 10 cm of the drive line, for attachment to the driver outside of the patient, is not covered. During implantation, usually 3–15 cm of the polyester velour on the drive line is left exterior to the skin exit site. This exterior polyester velour results in continuous accumulations of blood, serum, and persistent dampness on this exteriorized fabric. The utilization of the noded design of the present invention would minimize or prevent this problem.

In the preferred embodiment of this example, six nodes would be placed, as previously described, on the noded cuff in the region of the drive live corresponding to the range of anticipated skin exit site locations. Each node is preferably about 1–2 mm in width and the adjacent cuff segments are preferably about 1–1.5 cm long. The nodes are preferably full-depth nodes. The multiple nodes allows for adjustability and placement of a selected node at the skin exit site. The wicking effect in the noded cuff portion which is adjacent, and exterior to, the node/skin exit site interface will be limited to the length of the adjacent cuff segment, i.e., 1.5 cm or less. Moreover, once the dermis and epidermis migrate into the node as shown in FIG. 9B, even this wicking effect is almost totally eliminated. In addition, the cuff segment immediately adjacent, and exterior to, the node interfacing with the skin exit site may be removed after stable healing of the interface has been achieved. The remaining exterior nodes may also be removed, if desired, however, the most important area for wicking is at the immediately adjacent and exterior cuff segment.

Similar applications are possible for other devices. For example, as described above, a total artificial heart employing two exiting drive lines could employ the noded cuff of the present invention on both lines. Electric total artificial hearts may have only one drive line. The size of the line varies, however, depending on whether or not an internal volume compensator is used. For heart assist applications, either single or biventricular, similar designs are utilized. Some of these designs utilize vent tubes of silicone rubber with Dacron velours or woven fabrics. Some utilize polyurethanes with polyester velours or woven fabrics. All could benefit form the noded design.

The present invention may be embodied in other specific forms without departing from its spirit or essential characteristics. It is to be understood and appreciated from the general and specific teachings herein that the devices proposed in the figures are not meant to be limited to any specific prosthesis/tissue opening site interface. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed and desired to be secured by United States Letters Patent is:

1. A cuff for stabilizing a prosthetic device at an interface with a tissue opening site, comprising:
   a first cuff segment adapted for placement on a prosthetic device adjacent and internal to a tissue opening site, and a second cuff segment adapted for placement on the prosthetic device adjacent and external to the tissue opening site;
      each of said first and second cuff segments composed of a porous material permitting ingrowth of surrounding tissue into the porous material, each of said cuff segments capable of extending outwardly from a surface of the prosthetic device, wherein said second cuff segment is capable of being stripped from the prosthetic device while leaving said first cuff segment in place without disruption of the prosthetic device and tissue opening site interface; and
   a node defined by a space between said first and second cuff segments for tissue ingrowth at the tissue opening site;
      said node having a first side wall and a second side wall and a node termination between said first and second side walls at an innermost depth of said node;
   wherein said first side wall is defined by a side of said first cuff segment and said second side wall is defined by a side of said second cuff segment.
2. A cuff as defined in claim 1 wherein said first and second cuff segments are spaced apart such that said node is defined by a fixed space between said cuff segments.

3. A cuff as defined in claim 1 wherein at least an outer portion of at least one of said cuff segments is flexible and said first and second cuff segments are touching such that said node is defined by a space formed by flexing said cuff segment directionally away from the other cuff segment.

4. A cuff as defined in claim 1 wherein said first and said second cuff segments are flexible and said first and second cuff segments are touching such that said node is defined by a space formed by flexing said cuff segments directionally away from each other.

5. A cuff as defined in claim 1 wherein said node is a full-depth node such that said node termination is defined by said surface of said underlying prosthetic device.

6. A cuff as defined in claim 1 wherein said node is a partial-depth node such that said node termination is defined by material that extends outwardly from said surface of said underlying prosthetic device, said outward extension of said node termination being less than the outward extension of said first and second cuff segments.

7. A cuff as defined in claim 6 wherein said material comprises a porous material.

8. A cuff as defined in claim 1 wherein said innermost depth of said node is selected to facilitate migration of adjacent tissue to the node termination.

9. A cuff as defined in claim 1 wherein said node has a depth in the range of about 5 microns to about 3.5 mm.

10. A cuff as defined in claim 1 wherein said node has a width in the range of about 0.25 mm to about 2.5 mm.

11. A cuff as defined in claim 1 wherein said first side wall and said second side wall are symmetrically contoured.

12. A cuff as defined in claim 1 wherein said first side wall and said second side wall are asymmetrically contoured.

13. A cuff as defined in claim 1 wherein at least one of said first side wall or said second side wall is perpendicular to said surface of said underlying prosthetic device.

14. A cuff as defined in claim 1 wherein at least one of said first side wall or said second side wall is angled with respect to said surface of said underlying prosthetic device.

15. A cuff as defined in claim 1 wherein at least one of said first side wall or said second side wall is curved with respect to said surface of said underlying prosthetic device.

16. A cuff as defined in claim 1 further comprising a plurality of nodes formed along the cuff.

17. A noded cuff for stabilizing a prosthetic device at an interface with a tissue opening site, comprising:
   at least a first cuff segment adapted for placement on a prosthetic device adjacent and internal to a tissue opening site, and a second cuff segment adapted for placement on the prosthetic device adjacent and external to the tissue opening site;
      each of said cuff segments composed of a porous material permitting ingrowth of surrounding tissue into the material, said cuff segments capable of extending outwardly from a surface of the prosthetic device, wherein said second cuff segment is capable of being stripped from the prosthetic device while leaving said first cuff segment in place without disruption of the prosthetic device and tissue opening site interface; and
   at least one node defined by a space between said first and second cuff segments for tissue ingrowth at the tissue opening site,
      said node having a first side wall and an opposite second side wall and a node termination between said first and second side walls at an innermost depth of said node,
   wherein said first side wall is defined by a side of said first cuff segment and said second side wall is defined by a side of said second cuff segment, said first side wall having a first concave surface and said second side wall having an opposing second concave surface facing the first concave surface.

18. A noded cuff for stabilizing a prosthetic device at an interface with a tissue opening site, comprising:
   at least a first cuff segment adapted for placement on a prosthetic device adjacent and internal to a tissue opening site, and a second cuff segment adapted for placement on the prosthetic device adjacent and external to the tissue opening site;
      each of said cuff segments composed of a porous material permitting ingrowth of surrounding tissue into the material, said cuff segments capable of extending outwardly from a surface of the prosthetic device, wherein said second cuff segment is capable of being stripped from the prosthetic device while leaving said first cuff segment in place without disruption of the prosthetic device and tissue opening site interface; and
   at least one node defined by a space between said first and second cuff segments for tissue ingrowth at the tissue opening site,
      said node having a first side wall and an opposite second side wall and a node termination between said first and second side walls at an innermost depth of said node,
   wherein said first side wall is defined by a side of said first cuff segment and said second side wall is defined by a side of said second cuff segment, said first side wall having a first surface that is substantially perpendicular with respect to the surface of the prosthetic device and said second side wall having an opposing second surface that is convex.

19. A noded cuff for stabilizing a prosthetic device at an interface with a tissue opening site, comprising:
   at least a first cuff segment adapted for placement on a prosthetic device adjacent and internal to a tissue opening site, and a second cuff segment adapted for placement on the prosthetic device adjacent and external to the tissue opening site;
      each of said cuff segments composed of a porous material permitting ingrowth of surrounding tissue into the material, said cuff segments capable of extending outwardly from a surface of the prosthetic device, wherein said second cuff segment is capable of being stripped from the prosthetic device while leaving said first cuff segment in place without disruption of the prosthetic device and tissue opening site interface; and
   at least one node defined by a space between said first and second cuff segments for tissue ingrowth at the tissue opening site,
      said node having a first side wall and an opposite second side wall and a node termination between said first and second side walls at an innermost depth of said node,
   wherein said first side wall is defined by a side of said first cuff segment and said second side wall is defined by a side of said second cuff segment, said first side wall having a first surface with a notch formed therein for receiving the prosthetic device and said second side wall having an opposing second surface that is convex.

20. A noded cuff for stabilizing a prosthetic device at an interface with a tissue opening site, comprising:
   at least a first cuff segment adapted for placement on a prosthetic device adjacent and internal to a tissue opening site, and a second cuff segment adapted for placement on the prosthetic device adjacent and external to the tissue opening site;

each of said cuff segments composed of a porous material permitting ingrowth of surrounding tissue into the material, said cuff segments capable of extending outwardly from a surface of the prosthetic device, wherein said second cuff segment is capable of being stripped from the prosthetic device while leaving said first cuff segment in place without disruption of the prosthetic device and tissue opening site interface; and at least one node defined by a space between said first and second cuff segments for tissue ingrowth at the tissue opening site, said node having a first side wall and an opposite second side wall and a node termination between said first and second side walls at an innermost depth of said node, wherein said first side wall is defined by a side of said first cuff segment and said second side wall is defined by a side of said second cuff segment, said first side wall having a first surface that is angled with respect to the surface of the prosthetic device and said second side wall having an opposing second surface that is angled with respect to the surface of the prosthetic device such that the first and second surfaces are substantially parallel to each other.

* * * * *